(12) United States Patent
Kinnunen

(10) Patent No.: US 7,343,784 B2
(45) Date of Patent: Mar. 18, 2008

(54) METHOD AND DEVICE FOR FORMING A LIQUID—LIQUID INTERFACE, ESPECIALLY FOR SURFACE TENSION MEASUREMENT

(76) Inventor: Paavo Kinnunen, Punarinnantie 4, FI-02660 Espoo (FI)

( * ) Notice: Subject to any disclaimer, the term of this patent is extended or adjusted under 35 U.S.C. 154(b) by 243 days.

(21) Appl. No.: 11/167,252

(22) Filed: Jun. 28, 2005

(65) Prior Publication Data

US 2006/0288761 A1    Dec. 28, 2006

(51) Int. Cl.
*G01N 13/00* (2006.01)
(52) U.S. Cl. ..................... 73/64.48
(58) Field of Classification Search ............ 73/64.48, 73/64.49; 446/7, 8, 10, 13; 472/57, 71; 232/1 D
See application file for complete search history.

(56) References Cited

U.S. PATENT DOCUMENTS

| 1,804,733 | A | * | 5/1931 | Balson | 232/4 R |
| 5,269,176 | A | * | 12/1993 | Hool | 73/64.52 |
| 5,394,740 | A | * | 3/1995 | Schramm et al. | 73/64.48 |
| 2006/0275184 | A1 | * | 12/2006 | Furukawa et al. | 422/129 |

FOREIGN PATENT DOCUMENTS

| GB | 2265222 A | * | 9/1993 |
| JP | 06074889 A | * | 3/1994 |
| SU | 1052938 A | * | 11/1983 |
| WO | WO9423280 A1 | * | 10/1994 |

* cited by examiner

*Primary Examiner*—Hezron Williams
*Assistant Examiner*—John Fitzgerald
(74) *Attorney, Agent, or Firm*—Armstrong, Kratz, Quintos, Hanson & Brooks, LLP

(57) ABSTRACT

The present invention is directed to a method and a device for forming an interface between a first and a second essentially immiscible liquid, especially for the measurement of the surface tension at said interface. According to the invention, a volume of the first liquid is added to a first well having a closed bottom, walls and an upper opening in a horizontal surface. A volume of the second liquid is added to a second well, e.g. in the form of a bore or a sleeve having an upper well opening and a lower well opening which lower well opening rests in a sealing relationship on the said horizontal surface, the said surface closing the lower opening, but in sliding engagement therewith. The lower opening of the second well is brought into alignment with the upper opening of the first well, thus depositing the volume of the second liquid on top of the surface of the volume of the first liquid, to form the desired liquid-liquid interface.

38 Claims, 2 Drawing Sheets

METHOD AND DEVICE FOR FORMING A LIQUID—LIQUID INTERFACE, ESPECIALLY FOR SURFACE TENSION MEASUREMENT

FIELD OF THE INVENTION

The present invention generally relates to a method for forming an interface between two essentially immiscible liquids, especially for the purpose of measuring the surface tension at said interface. The invention also concerns a device for forming such an interface as well as an apparatus for measuring the surface tension of said interface. The invention can be used for measuring the surface tension and the emulsification behavior between two essentially immiscible liquids, such as an oil and an aqueous solution. The invention can also be used for determining the effect of e.g. surface active substances on the surface tension at said interface. The invention is particularly useful for measuring the effect of surface active agents and detergents on oily or fatty substances at an oil-water interface.

BACKGROUND OF THE INVENTION

The surface tension of a liquid can be measured for example by measuring the force applied to a probe placed in the interface between the said liquid and a gas, typically air. Such a probe can be in the form of a thin platinum plate such as a Wilhelmy plate, which is placed in the said interface. An alternative construction for the probe is in the form of a small diameter metal wire, for example a du Nouy ring.

A change in the surface tension is evidenced as a change in the amount of liquid adhered to the probe. When the surface tension of the liquid decreases, the amount adhered to the probe decreases linearly, and vice versa. The liquid adhered exerts a vertical force on the probe, which can be detected using a microbalance. Methods for measuring the surface tension at an air/water interface are described in WO 02/055996, entitled "Method for measuring the surface tension of an aqueous solution" and in WO 2004/025277, entitled "Method for surface tension measurement" which are included herein for reference.

In addition to measuring the surface tension at an interface between a liquid and a gas, such as air, there is a need for measuring the surface tension, and changes in the surface tension, at an interface between liquids that are essentially immiscible. Such information can be of importance for example in order to establish the emulsification properties of surfactants and detergents. When developing detergents it is essential to know how rapidly or effectively the detergent will emulsify or dissolve fat or oil, i.e. how effectively the fat and oil-like substances will be removed, for example during a washing operation. Such effects can be measured by measuring changes taking place in the surface tension at an interface between two liquids, such as an oil and an aqueous solution containing said detergent.

A problem has, however, been associated with the proper formation of an interface between the liquids which will allow for a rapid, correct and sensitive measurement of the surface tension and any changes therein. It would also be desirable to develop a system which would allow for rapid and efficient interface formation and surface tension measurement on a large-scale or screening basis, to be used for example in product development such as for the assessment of the surface active properties of various products, typically dissolved in one of the liquids being assessed. The said system could also be a useful tool in research relating to the study of kinetics between liquids.

SUMMARY OF THE INVENTION

In its broadest sense, the invention concerns a method and a device for forming an interface between a first and a second, essentially immiscible liquid, the method comprising the steps of adding a volume of the first liquid to a first or lower well, the well having a closed bottom portion, and a wall portion or portions extending from the bottom portion to define an upper well opening, adding a volume of the second liquid to a second or upper well having a wall portion or portions extending from an upper well opening to a lower well opening, the lower opening of the said well resting on a horizontal surface, said horizontal surface forming a closed bottom portion for the lower opening of the second well, moving the upper well and the said horizontal surface relatively each other, to open the lower opening of the upper well to provide a passage therethrough when the first well is in alignment with the second well, so as to deposit the second liquid onto the surface of the first liquid, to provide an interface between the first and the second liquid.

When the method is used for measuring the surface tension of the interface, the method comprises the additional steps of introducing a probe into the interface, and measuring the surface tension of the interface.

An object of the invention is more specifically a method for forming an interface between a first and a second, essentially immiscible liquid, comprising the steps of adding a volume of the first liquid in a first or lower well provided in a body having a horizontal surface, the well having a closed bottom portion, and a wall portion or portions extending from the bottom portion to define a well opening, adding a volume of the second liquid in a second or upper well having a wall portion or portions extending from an upper well opening to a lower well opening, the lower well opening, in a first position, being adapted to be sealed by the said horizontal surface, and moving the upper well so sealed and the said surface relatively each other from the said first position to a second position so as to align the lower opening of the upper well with the upper opening of the lower well, to deposit the second liquid on top of the first liquid and to provide an interface between the first and the second liquid.

Another object of the invention is a method for measuring the surface tension at an interface between a first and a second, essentially immiscible liquid formed according to the method described above. The method for measuring the surface tension comprises the additional steps of introducing a probe into the interface so formed and measuring the surface tension at the interface.

The invention is also directed to a device and an apparatus for carrying out said methods. The device according to the invention for forming the interface comprises a body having a horizontal surface, the body being provided with a first or lower well for receiving a volume of the first liquid, the well having a closed bottom portion, and a wall portion or portions extending from the bottom portion to define a well opening, and a second or upper well for receiving a volume of the second liquid having a wall portion or portions extending from an upper well opening to a lower well opening, which lower well opening is adapted to be sealable by the horizontal surface and movable relatively thereto, to provide a passage for the second liquid through the well opening to deposit the second liquid onto the surface of the first liquid.

According to a preferred embodiment, the lower well opening, in a first position, is adapted to be sealable by the horizontal surface, the upper well so sealed and the said body being movable relatively each other from the said first position where the horizontal surface of the body closes the lower opening of the upper well, to a second position where the lower opening of the upper well is aligned with the upper opening of the lower well in the first body.

According to a preferred embodiment the well opening of the lower well is in the horizontal surface of the body, and the lower well opening of the upper well is defined by a rim which is adapted to rest on the horizontal surface and to move relatively the said body in sliding engagement with the said surface.

According to a preferred embodiment, the upper well is provided in, or forms part of, a further or second body adapted to rest with a horizontal surface containing said lower opening in a sealing manner against the horizontal surface of the first mentioned body, in sliding engagement therewith. The well can thus be in the form of a bore or a sleeve, the walls of which extend from the lower opening to the upper opening. In one embodiment, the well can be in the form of a bore extending from the horizontal surface containing the lower opening, to an upper surface in the said second body containing the upper opening of the bore. According to a further preferred embodiment, both the first mentioned body and the further body are each provided with a lower horizontal surface and an upper horizontal surface.

The invention also concerns an apparatus for measuring the surface tension between two essentially immiscible liquids. The apparatus comprises the above described device for forming an interface between the first and the second liquid, means for aligning the upper and the lower well, and means for introducing a probe into the liquid-liquid interface so formed, as well as means for measuring the surface tension at the liquid-liquid interface.

BRIEF DESCRIPTION OF THE DRAWINGS

FIG. 1 shows a device according to a preferred embodiment of the invention.

DETAILED DESCRIPTION OF THE INVENTION

The invention is especially set out to solve the problem of measuring the surface tension at an interface between two essentially immiscible liquids. The term 'essentially immiscible liquids' means liquids that do not easily mix or dissolve. This means that the said liquids can be characterized as being mutually insoluble, very poorly soluble or poorly soluble. Essential is, however, that the said liquids do not essentially mix or dissolve at least not within the time frame reserved for carrying out the surface tension measurement. According to the present invention, the surface tension measurement is typically carried out rapidly after the interface formation.

Usually the surface tension measurement will be carried out within appr. 60 seconds after interface formation, and more typically within at the most 20 seconds from the formation of the interface. However, even shorter times can be used. As an example, an aqueous solution and an oil can be mentioned as essentially immiscible liquids. Also liquids that will eventually mix at least to some degree are of interest. As an example of this oil and an aqueous detergent solution can be mentioned. Other liquid systems of interest are aqueous solutions and higher alcohols, such as octanol, which can be used for example to measure the surface active properties of various substances such as drugs, or aqueous solutions and gasoline, for use for example in the development of oil recovery systems.

Figure 1A:
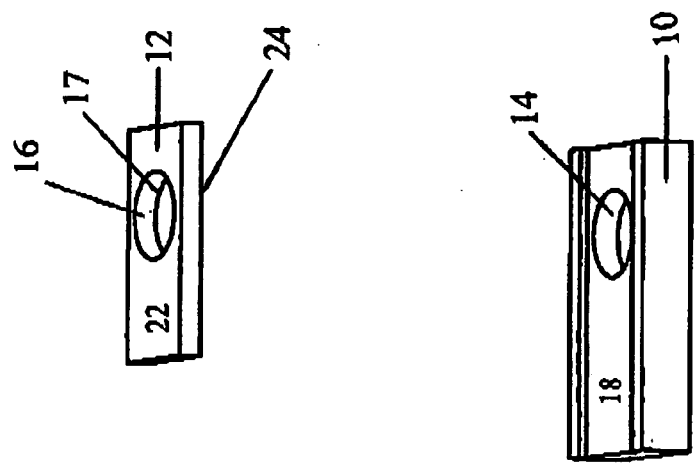
FIG. 1a shows the separate parts of the device and FIG. 1b shows the assembled device, where the second body is made to slide on top of the first body.
Figure 1B:
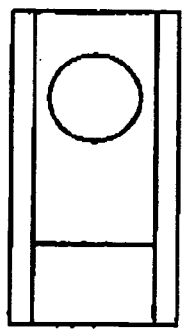
Figure 1B:
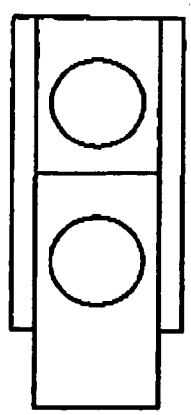
Figure 1B:
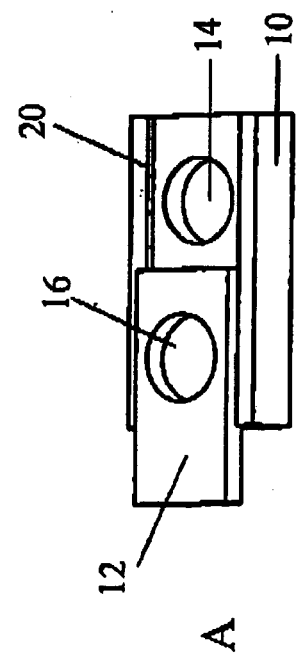

In the following the invention will be discussed with reference to the drawing. In the drawing, FIG. 1a and FIG. 1b show a preferred embodiment of the invention comprising a first or lower body 10 with a first or lower well 14 for receiving a volume of a first liquid. The opening of the well 14 lies in the upper horizontal surface of the body 10. The device also comprises a second upper well 16 in the form of a bore having a lower rim 17, the bore extending from an upper horizontal surface 22 to a lower horizontal surface 24 provided in a second or upper body 12. The lower surface 24, including the opening of the well 16 and its rim 17, is adapted to rest on the upper horizontal surface 18 of the first body 10, in sliding engagement therewith. In this embodiment the upper surface 18 of the first mentioned body 10 will seal off the lower opening of the bore and form a closed bottom therefor, thus forming a well 16 that can receive and contain a volume of the second liquid prior to forming the interface with the first liquid in the lower well 14. This relative position of the wells 14 and 16 wherein the said wells are in a mutually non-aligned position allowing a suitable volume of liquid to be introduced into the respective upper and lower wells, is indicated with the letter "A" in FIG. 1b. The volume of liquid added to the lower well is preferably so dimensioned that the surface of the liquid will be flush or essentially flush with, or even bulge above the upper horizontal surface 18 of the body 10 so as avoid any distance between the upper surface of the first volume of liquid in the first well and the lower opening of the second well. Any superfluous liquid in the lower well will be swept or cut away by the subsequent relative movement of the wells, as explained below.

The upper and lower wells can have essentially any shape or form as long as an alignment of the wells allows for the formation of an interface between the liquids to be assessed. According to a preferred embodiment of the invention both the lower opening of the upper well 16, or bore, and the upper part or upper opening of the lower well 14 have identical horizontal cross sections. Preferably the wells are in the form of a cylinder and thus the cross-sections are essentially circular. In this case the proper alignment of the wells in the said second position will result in a combined well the height of which will be defined by the combined heights of the lower and upper wells, respectively, the liquid-liquid interface being formed essentially at the point of contact between the upper opening of the lower well, and the lower opening of the upper well or bore. However, the wells, such as the lower well, can also be in the form of an inverted, optionally truncated cone or pyramid, having a circular or square horizontal cross-section; the upper well can then take any shape that will allow the formation of an interface and measurement of the surface tension. Thus, for example, a lower well in the form of an inverted optionally truncated cone, can be used in combination with a cylindrical upper well or bore.

After a volume of liquid has been added to the lower and upper wells, respectively, the bodies 12 and 10 will be moved relatively each other, along the respective surfaces 18 and 24 while in sliding engagement, from a position where the lower opening of the well 16 is sealed against the top of the surface 18, to a second position where the wells 16 and 14 are in an aligned relationship, the upper well 16 on top of the lower well 14, that is to the position marked with the letter "B" in FIG. 1b. Advantageously the movement of the upper and lower bodies can be guided with suitable guiding or control means, which in the embodiment shown are comprised of guide rails 20 formed on the lower body 10 which suitably cooperate with suitable means on the upper body 12. It is, however, understood that any means which are suitable for controlling the relative movement between the bodies 10 and 12 can be used. When the bodies 10 and 12 with corresponding wells 14 and 16 have reached the position indicated by the letter "B" in the FIG. 1b, where the lower opening of the second well no longer rests on the horizontal surface of the first body, the liquid in the upper well will have been released, through the lower opening in the second well, onto the surface of the liquid in the lower well, to form the desired liquid-liquid interface.

The liquids which are to form the interface will not only be essentially immiscible but will typically have different densities. According to the invention, the liquids are added to the wells so that the liquid with the lower density is added to the upper well and the liquid with the higher density is added to the lower well. This will result in a proper and instant formation of the interface between the liquids after alignment of the wells and deposition of the lighter liquid on top of the denser liquid, without any rearrangement of the liquids after deposition thereof.

The bodies 10 and 12 can be made of any material suitable for the purpose, that is of a material which is sufficiently mechanically and dimensionally stable. Such a material can be typically a suitable plastics material, such as a polyacetal resin known as Delrin®.

Although not shown in FIG. 1, according to an embodiment of the invention, the inside wall and bottom portions of the lower well 14 and optionally the upper horizontal surface 18 of the body 10 can carry a surface lining in the form of a disposable insert. According to the embodiment, also the inside walls of the bore 16 and optionally the lower horizontal surface 24 of the body 12 can carry a surface lining in the form of a disposable insert. The disposable insert is preferably formed of a hydrophobic material, such as a polyolefin polymer. This embodiment has the advantage that the parts which come in contact with the liquids, and optionally also the sliding surfaces of the bodies 10, 12 carrying the wells 14, 16, can be removed and discarded after use, thus eliminating or at least facilitating washing of the wells after use, and resulting in an especially cost and time-effective solution.

According to another preferred embodiment, at least one of the engaging horizontal surfaces 18, 24 of the first and second body is coated by a hydrophobic, optionally a low friction material, such as polytetrafluoroethylene polymer, to reduce any wetting of the surfaces and to provide for a smooth sliding relative movement of the bodies in order to facilitate a rapid alignment of the wells and for a proper formation of the interface between the liquids in the wells 14, 16. According to a variation of this embodiment, a separate plate or sheet of such a material can be used between the bodies instead of a coating. According to an embodiment, the said plate or sheet can be movably placed between the first 10 and second body 12, the plate or sheet advantageously having a shape essentially corresponding to that of the first 10 or second body 12, the said sheet having a hole of a shape and size advantageously corresponding to the horizontal cross-section of the upper opening of the lower well and/or to that of the lower opening of the upper well. According to this embodiment, the interface can be formed according to the invention by adding a volume of the first liquid to the lower well and a volume of the second liquid to the upper well, the first and the second liquids in the wells being initially separated by means of the said intermediate sheet when the wells are in the aligned position, and in a subsequent step moving the said sheet so as to align the hole in the sheet with the upper opening of the lower well and the lower opening of the upper well, to deposit the second liquid onto the first liquid to form the desired interface.

For measuring of the surface tension at the interface a suitable probe is used. Any one of the probes typically used for example for liquid/gas interfaces can be used, and as such are known to the person skilled in the art. Advantageously the probe is wet by a liquid corresponding to that added to the lower well 14 before introducing the probe into the liquid in the upper well 16. By wetting the probe in this manner it is possible to avoid a situation where the liquid in the upper well 16 adheres to the probe, which could interfere with the measurement and give inaccurate measurement results. In a preferred embodiment, the probe is in a suitable manner connected to a micro-scale or balance for measuring the surface tension or changes in the surface tension at the interface. In a preferred embodiment of the invention the probe is a Cr—Ni wire probe.

The probe is advantageously introduced in the liquid in the upper well 16, in close proximity to the bottom thereof, prior to forming the interface, that is when the device is in the position marked with the letter "A" in FIG. 1b. In practice this is done by suspending the probe to a position very close to the bottom of the well 16, and optionally in a second step retracting the probe somewhat. After alignment of the wells and the formation of the interface, the probe is then suspended into the interface formed, allowing for a rapid measurement and registration of the surface tension at the interface.

Naturally the surface tension at the interface is measured as soon as only possible after the interface is formed, but at least before any changes take place at the interface which are detrimental for obtaining correct measurement results. For interfaces formed between an aqueous detergent solution and an oil the changes in the surface tension that are of interest are typically measured in a time span which is less than approximately 20 s from forming of the interface. In cases where the liquids in question are immiscible and there is no essential danger of detrimental dissolution changes taking place in the interface, the said allowable time span can of course be longer, should there be a need therefor.

As stated earlier, in one preferred embodiment the wells are cylindrically shaped. The wells are typically small and can have a diameter of 5–50 mm, preferably 10–20 mm. A relatively small well size is preferred to minimize the amounts of solution needed for the measurement and is also easier to handle. An apparatus for measuring the surface tension, for example for screening purposes involving the measurement of a large number of sample systems, will typically contain an array or series of devices, either arranged separately, each device containing a body with a lower well cooperating with an upper well in a second body, as shown in the embodiment of the drawing. Alternatively it is conceivable that the lower body contains an array of lower wells arranged in the same body, which array of lower wells can cooperate with a corresponding number of upper wells or bores arranged in a single upper body, or each lower well can cooperate with its own upper well arranged in its corresponding own body. According to a variation of this embodiment, the upper wells can also be in the form of an array of wells included in the same body, each well cooperating with its corresponding lower well, either arranged in its own separate or in a common lower body. In such an arrangement, the interface formation and optionally the surface tension measurement can be carried out simultaneously in some or in all the well pairs, after aligning the appropriate upper and the lower wells. Such an arrangement can provide a very efficient means of carrying out a large number of measurements.

Figure 2:
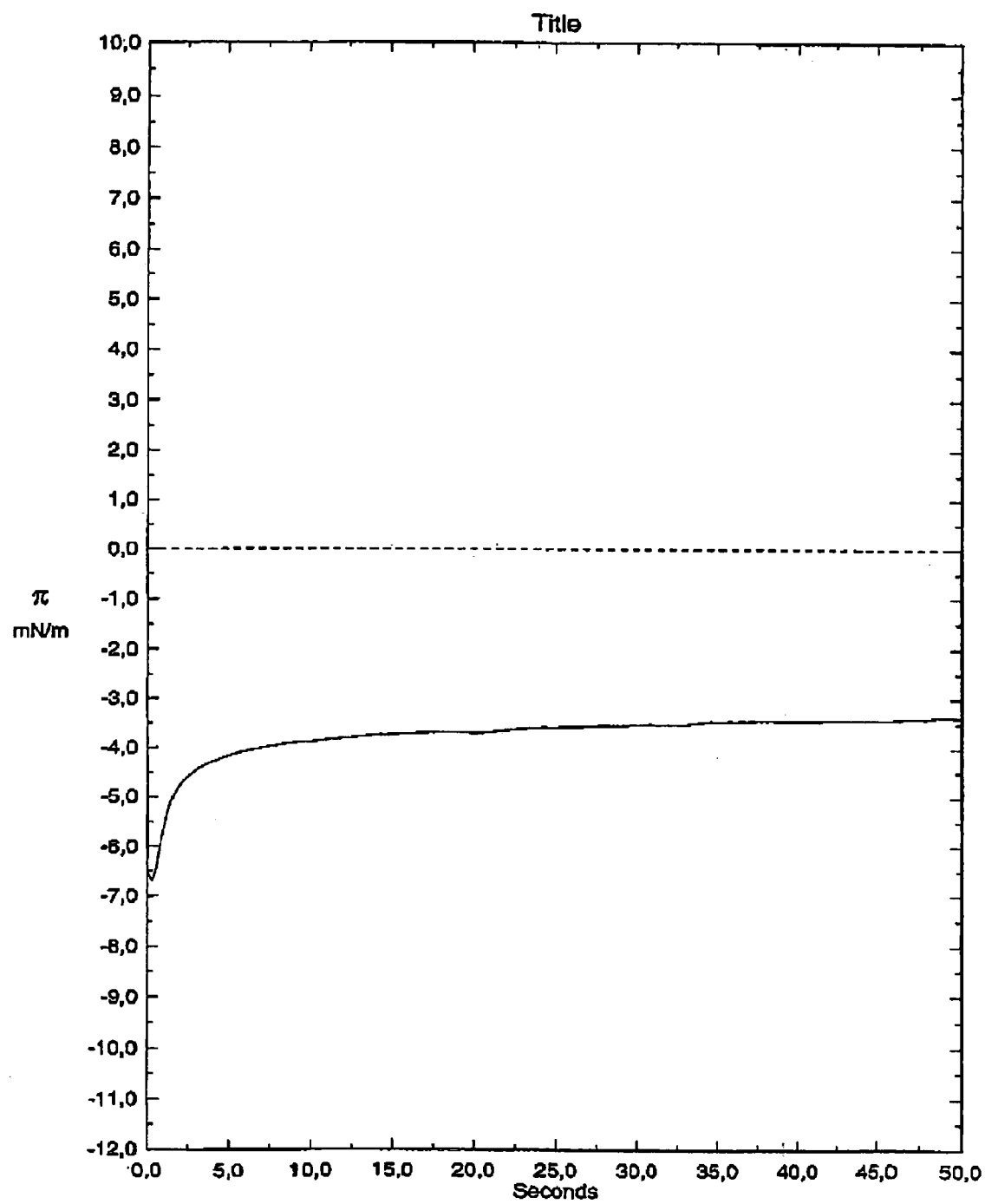
FIG. 2 shows results from measurements made according to the invention where the surface tension is measured at the interface between an oil and an aqueous detergent solution.

FIG. 2 shows the results of measuring the surface tension at the interface between an aqueous detergent solution and an oil. The aqueous solution contained 10% of sodium dodecyl sulfate in a sodium sulfate buffer at pH 10, and this aqueous solution was added to the lower well. The oil used in the test was canola oil added to the upper well. The surface tension at the interface was measured using a probe and a micro-scale and registered for a period of up to 50 seconds. It can be seen that the change in surface tension between the oil and water quickly reaches an equilibrium, meaning the surface active properties of the detergent are effective rapidly after contact with the oil.

The invention claimed is:

1. A method for measuring the surface tension at an interface between a first and a second, essentially immiscible liquid, comprising the steps of:
    adding a volume of the first liquid in a first or lower well provided in a body having a horizontal surface, the well having a closed bottom portion, and a wall portion or portions extending from the bottom portion to define a well opening,
    adding a volume of the second liquid in a second or upper well having a wall portion or portions extending from an upper well opening to a lower well opening, which lower opening, in a first position, is adapted to be sealed by the said horizontal surface,
    moving the upper well so sealed and the said surface relatively each other from the said first position to a second position so as to align the lower opening of the upper well with the upper opening of the lower well, to deposit the second liquid on top of the first liquid and to provide an interface between the first and the second liquid,
    introducing a probe into the interface; and
    measuring the surface tension of the interface.

2. The method according to claim 1, wherein the first and the second liquid have different densities, and the liquid having the lower density is added to the upper well.

3. The method according to claim 1, wherein one of the first and second liquid is an aqueous solution and the other is a higher alcohol such as octanol.

4. The method according to claim 1, wherein the wells are cylindrically shaped and have a diameter of 5–50 mm, preferably 10–20 mm.

5. The method according to claim 1, wherein the probe is introduced in the liquid in the upper well, in close proximity to the bottom thereof, prior to forming the interface.

6. The method according to claim 1, wherein the probe is wet by a liquid corresponding to that added to the lower well before introducing the same into the liquid in the upper well.

7. The method according to claim 1, wherein the surface tension is measured at a time span of less than 20 s from forming of the interface.

8. The method according to claim 1, wherein the well opening of the lower well is in the horizontal surface, and the lower well opening of the upper well is defined by a rim which is adapted to rest on the horizontal surface and to move relatively the said body in sliding engagement with the said surface.

9. The method according to claim 8, wherein the second upper well is provided in, or forms a part of, a further or second body having a horizontal surface containing the lower opening of the said well and adapted to rest on the horizontal surface of the said first mentioned body, in sliding engagement therewith.

10. The method according to claim 9, wherein the upper well is in the form of a bore extending from the horizontal surface of the second body to an upper surface containing the upper well opening.

11. The method according to claim 9, wherein at least one of the engaging horizontal surfaces of the first mentioned and the further body is coated by a hydrophobic, optionally low friction material, such as polytetrafluoroethylene polymer.

12. The method according to claim 9, wherein the walls of the upper well and optionally the horizontal surface of the further body carries a lining in the form of a disposable insert.

13. The method according to claim 12, wherein the disposable insert is formed of a hydrophobic material, preferable a polyolefin polymer.

14. The method according to claim 1, wherein the wall and bottom portions of the lower well and optionally the horizontal surface of the first mentioned body carries a lining in the form of a disposable insert.

15. The method according to claim 14, wherein the disposable insert is formed of a hydrophobic material, preferably a polyolefin polymer.

16. The method according to claim 1, wherein the probe is connected to a micro-scale, for measuring the surface tension.

17. The method according to claim 16, wherein the probe is a Cr—Ni wire probe.

18. The method according to claim 1 wherein the first liquid is an aqueous solution and the second liquid is an oil.

19. The method according to claim 18 wherein the first liquid is an aqueous detergent solution.

20. A method for forming an interface between a first and a second, essentially immiscible liquid, the method comprising the steps of
    adding a volume of the first liquid to a first or lower well, the well having a closed bottom portion, and a wall portion or portions extending from the bottom portion to define an upper well opening,
    adding a volume of the second liquid to a second or upper well having a wall portion or portions extending from an upper well opening to a lower well opening, the lower opening of the said well resting on a horizontal surface, said horizontal surface forming a closed bottom portion for the lower opening of the second well,
    moving the upper well and the said horizontal surface relatively each other, to provide a passage through the lower opening when the first well is in alignment with the second well, so as to deposit the second liquid onto the surface of the first liquid, to provide an interface between the first and the second liquid.

21. A method for forming an interface between a first and a second, essentially immiscible liquid, comprising the steps of:
    adding a volume of the first liquid in a first or lower well provided in a body having a horizontal surface, the well having a closed bottom portion, and a wall portion or portions extending from the bottom portion to define a well opening, adding a volume of the second liquid in a second or upper well having a wall portion or portions extending from an upper well opening to a lower well opening, which lower opening, in a first position, is adapted to be sealed by the said horizontal surface, moving the upper well so sealed and the said surface relatively each other from the said first position to a second position so as to align the lower opening of the upper well with the upper opening of the lower well, to deposit the second liquid on top of the first liquid and to provide an interface between the first and the second liquid.

22. The method according to claim 21 comprising the additional steps of introducing a probe into the interface and measuring the surface tension of the interface.

23. The method according to claim 21, wherein the well opening of the lower well is in the horizontal surface, and the lower well opening of the upper well is defined by a rim which is adapted to rest on the horizontal surface and to move relatively the said body in sliding engagement with the said surface.

24. The method according to claim 23, wherein the second upper well is provided in, or forms a part of, a further body having a horizontal surface containing the lower opening of the said well and adapted to rest on the horizontal surface of the said first mentioned body, in sliding engagement therewith.

25. Device for providing an interface between a first and a second essentially immiscible liquid, the device comprising a body having a horizontal surface, the body being provided with a first or lower well for receiving a volume of the first liquid, the well having a closed bottom portion, and a wall portion or portions extending from the bottom portion, the walls defining a well opening, a second or upper well for receiving a volume of the second liquid having a wall portion or portions extending from an upper well opening to a lower well opening, which lower well opening is adapted to be sealed by the said horizontal surface and movable relatively thereto, to provide a passage for the second liquid through the well opening to deposit onto the surface of the first liquid.

26. The device according to claim 25, wherein the lower opening of the upper well, in a first position, is adapted to be sealable by the horizontal surface, and the upper well and the said body being movable relatively each other, from the said first position where the horizontal surface of the body closes the lower opening of the upper well, to a second position where the lower opening of the upper well is aligned with the upper opening of the lower well in the first body.

27. The device according to claim 25, wherein the body containing the lower well has an upper horizontal surface containing the well opening and a lower horizontal surface.

28. Apparatus for measuring the surface tension of an interface between a first and a second essentially immiscible liquid, the apparatus comprising a device in accordance with claim 25 for forming the interface between the first and the second liquid, means for bringing the upper and the lower well in alignment, means for introducing a probe into the liquid-liquid interface so formed, and means for measuring the surface tension of the liquid-liquid interface.

29. The apparatus according to claim 28, wherein the probe is connected to a micro-scale for measuring the surface tension.

30. The apparatus according to claim 28, wherein the probe is a Cr—Ni wire probe.

31. The device according to claim 25, wherein the wall and bottom portions of the lower well and optionally the horizontal surface of the body carries a lining in the form of a disposable insert.

32. The device according to claim 31, wherein the disposable insert is formed of a hydrophobic material, preferably a polyolefin polymer.

33. The device according to claim 25, wherein the well opening of the lower well is in the horizontal surface, and the lower well opening of the upper well is defined by a rim which is adapted to rest on the horizontal surface and to move relatively the said body in sliding engagement with the said surface.

34. The device according to the claim 33, wherein the upper well is provided in, or forms part of, a further body having a horizontal surface containing the lower opening of the said well and adapted to rest on the horizontal surface of the first body, in sliding engagement therewith.

35. The device according to claim 34, wherein the upper well is in the form of a bore extending from the horizontal surface of the second body to an upper surface thereof containing the upper well opening.

36. The device according to claim 34, wherein at least one of the engaging horizontal surfaces of the said bodies is coated by a hydrophobic, optionally low friction material such as polytetrafluoroethylene polymer.

37. The device according to claim 34, wherein the bore and optionally the horizontal surface of the further body carries a lining in the form of a disposable insert.

38. The device according to claim 37, wherein the disposable insert is formed of a hydrophobic material, preferably a polyolefin polymer.

* * * * *